United States Patent [19]
Leng et al.

[11] Patent Number: 6,066,734
[45] Date of Patent: May 23, 2000

[54] CHLOROPYRIMIDINE PROCESS

[75] Inventors: Ronald B. Leng; Julie L. Maurer; James W. Ringer, all of Midland, Mich.

[73] Assignee: Dow AgroSciences LLC, Indianapolis, Ind.

[21] Appl. No.: 09/216,269

[22] Filed: Dec. 18, 1998

Related U.S. Application Data

[60] Provisional application No. 60/068,203, Dec. 19, 1997.

[51] Int. Cl.[7] ..................... C07D 239/30; C07D 239/32; C07D 239/52
[52] U.S. Cl. ................. 544/334; 544/313; 544/298; 544/315; 544/318; 544/319
[58] Field of Search ..................... 544/334, 313, 544/298, 315, 318, 319

[56] References Cited

U.S. PATENT DOCUMENTS

| | | | |
|---|---|---|---|
| 3,845,194 | 10/1974 | Somlo et al. | 423/300 |
| 5,057,517 | 10/1991 | Johnson et al. | 514/254 |
| 5,525,724 | 6/1996 | Hunds et al. | 544/334 |
| 5,563,270 | 10/1996 | Schwartz et al. | 544/330 |
| 5,677,453 | 10/1997 | Cramm et al. | 544/334 |
| 5,698,695 | 12/1997 | Appleton et al. | 544/330 |
| 5,719,285 | 2/1998 | Steffan | 544/334 |

FOREIGN PATENT DOCUMENTS

| | | |
|---|---|---|
| 0745593 A2 | 5/1996 | European Pat. Off. . |
| 0747364 A2 | 12/1996 | European Pat. Off. . |
| WO 96/23776 | 8/1996 | WIPO . |

OTHER PUBLICATIONS

Takeda Chem. Ind., Derwent Abstracts 89–136257 (Abstracting Japanese Patent Application No. 01083071, published Mar. 28, 1989).

*Primary Examiner*—John M. Ford
*Attorney, Agent, or Firm*—Craig E. Mixan; Kenneth L. Loertscher

[57] ABSTRACT

Chloropyrimidine compounds, such as 4,6-dichloro-2-ethoxypyrimidine, were prepared in good yield and good purity from the corresponding hydroxypyrimidine compounds in the absence of organic solvents and with a reduced amount of phosphorus oxychloride by carrying out the reaction in the presence of a trialkylamine compound and phosphorus trichloride. The additions of hydroxypyrimidine compound and trialkylamine compound could be made in segments. The chloropyrimidine compounds produced were recovered in an improved manner by adding chlorine to convert the chlorophosphoric acid by-products and phosphorus trichloride to phosphorus oxychloride, diluting the mixture with additional chloropyrimidine compound and removing the phosphorus oxychloride by distillation, combining the residue with water and a base, distilling the trialkylamine compound from the resulting mixture, and removing the aqueous phase.

14 Claims, No Drawings

CHLOROPYRIMIDINE PROCESS

CROSS-REFERENCE TO RELATED APPLICATIONS

This application claims the benefit of U.S. Provisional Application No. 60/068203, filed Dec. 19, 1997.

BACKGROUND OF THE INVENTION

The present invention relates to an improved process for producing chloropyrimidine compounds from hydroxypyrimidine compounds.

Chloropyrimidine compounds are valuable intermediates in the preparation of a wide variety of end use products, especially agricultural and pharmaceutical products. Such compounds, especially 2-, 4-, and 6-chloropyrimidine compounds, are typically prepared by the reaction of the corresponding hydroxypyrimidine compound with phosphorus oxychloride. The general process is described by D. J. Brown in "The Pyrimidines" from the monograph series "The Chemistry of Heterocyclic Compounds", pages 162–167 (1962) and many other well known publications. The process is sometimes carried out in the presence of a tertiary amine, which acts as an acid acceptor and a reaction promoter. The process as described in the art is, further, carried out in the presence of either a large excess of phosphorus oxychloride or of an organic solvent, such as acetonitrile or o-dichlorobenzene, which acts as a diluent to keep the reaction mixture fluid. The excess phosphorus oxychloride and/or organic solvent that is required increases the raw material cost of the chlorination process, makes expensive recycling of the diluent mandatory, and reduces the capacity of the production equipment.

In laboratory scale operations (for example, U.S. Pat. No. 5,057,517) and in the older art, the chloropyrimidine compounds produced by the reaction of an hydroxypyrimidine compound with phosphorus oxychloride are recovered by hydrolyzing the by-product chlorophosphoric acid compounds and excess phosphorus oxychloride with water and then removing the chloropyrimidine compound from the mixture obtained by filtration or extraction. A portion of the excess phosphorus oxychloride is sometimes removed by distillation before this operation. This procedure creates a large volume of undesirable aqueous phosphate waste. In recent years, the process for converting the by-product chlorophoshoric acids to phosphorus oxychloride by reaction with phosphorus pentachloride or with phosphorus trichloride and chlorine that is described, for example, in U.S. Pat. No. 3,845,194 has typically been used to reduce the cost and minimize the waste disposal problems. When this recovery process is employed, the phosphorus oxychloride reaction is generally carried out as described above and then, in a subsequent step, phosphorus pentachloride or phosphorus trichloride and chlorine are added. The phosphorus oxychloride produced in this manner and the excess used in the process are then separated from the mixture by distillation. A high boiling solvent, such as diphenyl ether, is sometimes added to facilitate the distillation. The desired chloropyrimidine compound is then recovered from the distillation residue by further distillation to recover the chloropyrimidine compound (EP 747364, published May 28, 1997), by filtration to remove the insoluble amine salts from the (liquid) chloropyrimidine compound either directly or after adding an organic solvent (U.S. Pat. No. 5,525,724), or by dilution with water followed by filtration, phase separation, or extraction with an organic solvent. The trialkylamine hydrochloride compound by-products formed as a result of these operations are typically recovered for recycle by basification. None of these recovery processes, however, is entirely satisfactory because of thermal decomposition, product losses and difficulties in the separations, and other yield reducing problems.

SUMMARY OF THE INVENTION

It has now been found that chloropyrimidine compounds can be made in good yield and good purity by the reaction of their corresponding hydroxypyrimidine compounds with phosphorus oxychloride in the absence of organic solvents and with a reduced amount of phosphorus oxychloride by carrying out the reaction in the presence of a trialkylamine compound and phosphorus trichloride. The chloropyrimidine compounds produced can, further, be recovered in an improved manner by adding chlorine to the reaction mixture obtained to convert the chlorophosphoric acid by-products to phosphorus oxychloride, diluting the mixture with an additional amount of the chloropyrimidine compound being produced and removing the phosphorus oxychloride by distillation, adding water and a base to the residue, distilling the trialkylamine compound from the resulting mixture under reduced pressure, and removing the aqueous phase.

The invention includes a process for the preparation of a chloropyrimidine compound of Formula I:

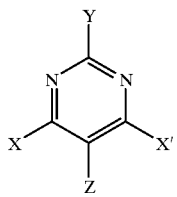

wherein

X and X' each, independently represents $C_1$–$C_4$ alkyl, $C_1$–$C_4$ fluoroalkyl, $C_1$–$C_4$ alkoxy, $C_1$–$C_4$ alkylthio, CN, or Cl with the proviso that at least one X and X' represents Cl;

Y represents $C_1$–$C_4$ alkyl, $C_1$–$C_4$ fluoroalkyl, $C_1$–$C_4$ alkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ alkylthio, CN, F, Cl, or Br which comprises contacting an hydroxypyrimidine compound of Formula II:

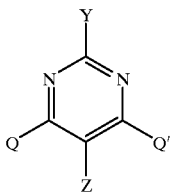

wherein

Q and Q' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, Cl, or OH with the proviso that at least one of Q and Q' represents OH;

Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br with, based on the number of moles of hydroxy group in the hydroxypyrimidine compound, at least about one to about two moles of phosphorus oxychloride, at least about one mole of phosphorus trichloride, and at least about one mole of a trialkylamine compound of Formula III:

$R_3N$ wherein each R independently represents a $C_1$–$C_8$ alkyl group and said trialkylamine compound contains up to about 15 carbon atoms and heating.

It is often most preferred to use about 1.5 moles of phosphorus oxychloride and about 1.01 to about 1.05 mole of phosphorus trichloride per mole of hydroxy group in the hydroxypyrimidine starting material. Triethylamine is a preferred trialkylamine compound. Temperatures of about 40° C. to about 100° C. are often preferred.

It is further typically preferred to carry out the preparative aspect of the invention in multiple segments; that is, by the consecutive steps of a) combining 20 to 80 percent of the total amount of hydroxypyrimidine compound used with the phosphorus oxychloride and phosphorus trichloride, b) adding the same percentage as in a) of the total amount of trialkylamine compound used and allowing the mixture to react for a period, c) adding another percentage of the total amount of hydroxypyrimidine compound, d) adding the same percentage as in c) of the total amount of trialkylamine compound and allowing the mixture to react for a period, and e) repeating steps c) and d) until the total amounts of hydroxypyrimidine and trialkylamine compound used have been added.

It is typically most preferred to add about 50 percent of the hydroxypyrimidine compound and of the trialkylamine compound in steps a) and b) and the remaining about 50 percent of each in steps c) and d).

The invention further includes a process for recovering a chloropyrimidine compound of Formula I:

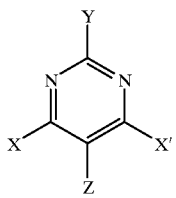

wherein

X and X' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl with the proviso that at least one X and X' represents Cl;

Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br from the mixture obtained by the reaction of an hydroxypyrimidine compound of Formula II:

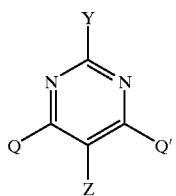

wherein

Q and Q' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, Cl, or OH with the proviso that at least one of Q and Q' represents OH;

Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br with phosphorus oxychloride and a trialkylamine compound of Formula III:

$R_3N$ wherein each R independently represents a $C_1$–$C_8$ alkyl group and said trialkylamine compound contains up to about 15 carbon atoms which process comprises the consecutive steps of a) converting the by-product chlorophosphoric acids in said mixture to phosphorus oxychloride by reaction with phosphorus trichloride and chlorine at about 30° C. to about 150° C., b) adding a supplemental amount of the chloropyrimidine compound being recovered and removing phosphorus oxychloride by distillation, c) combining the distillation residue with water and an alkali metal hydroxide base to obtain a two liquid phase system, the aqueous phase of which has a pH of about 11 or higher, d) removing the trialkylamine compound by distillation, and e) removing the aqueous phase.

It is generally preferred to employ the preparative and recovery aspects of the process of the invention in concert.

The process of the invention is advantageously applied to the preparation of 4,6-dichloro-2-ethoxypyrimidine from 4,6-dihydroxy-2-ethoxypyrimidine.

DETAILED DESCRIPTION OF THE INVENTION

The process of the present invention is generally concerned with the preparation of pyrimidine compounds having a chloro substituent in the 4- and/or 6-position from pyrimidine compounds having an hydroxy substituent in the 4- and/or 6-position. The compounds prepared may possess other substituents, including other chloro substituents. The chloropyrimidine compounds prepared include those of Formula I:

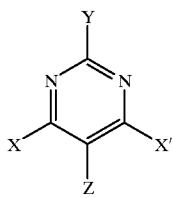

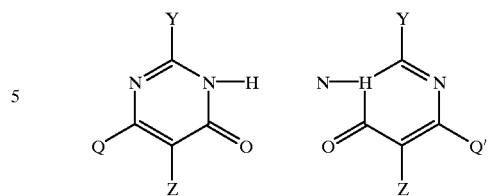

wherein X and X' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl with the proviso that at least one of X and X' represents Cl; Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br. Compounds of Formula I wherein both X and X' represent chloro are sometimes preferred products as are compounds wherein one of X and X' represents chloro and the other represents methyl. Compounds wherein Z represents H or F are often preferred. Compounds wherein Y represents methoxy or ethoxy are, further, often preferred. The process is especially suited to the preparation of 2-methoxy and 2-ethoxy chloropyrimidine compounds because such compounds typically are not stable under the reaction conditions required for related processes and poor results are often obtained. Compounds of Formula I wherein one of X and X' represents chloro and the other represents chloro or methyl; Y represents methoxy or ethoxy; and Z represents fluoro or hydrogen are typically more preferred products. The process of the invention is especially applicable to the preparation of 4,6-dichloro-2-ethoxypyrimidine, an intermediate that is useful in the preparation of valuable herbicides.

The hydroxypyrimidine compounds that serve as starting materials for the process include those of Formula II:

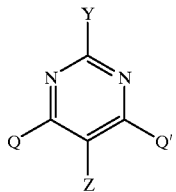

wherein Q and Q' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, Cl, or OH with the proviso that at least one of Q and Q' represents OH; Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br. The compounds of Formula II are alternatively depicted in the art as one of the keto isomers shown as Formula IIA:

The hydroxy and keto forms of the starting materials of Formula II as well as other possible keto forms bear a tautomeric relationship, exist in facile equilibrium, and are indistinguishable from a chemical reaction point of view. All references to hydroxypyrimidine compounds of Formula II herein expressly include the tautomeric forms of Formula IIA as well as all other possible tautomeric forms.

The preparative aspect of the process is generally carried out by combining a compound of Formula II with phosphorus oxychloride, phosphorus trichloride, and a trialkylamine compound and heating the mixture. A reaction mixture is produced that contains primarily the desired chloropyrimidine compound of Formula I along with other components believed to include trialkylamine salts of chlorophosphoric acids and anhydrides of chlorophosphoric acids.

It is generally preferred to employ at least about one to about two moles of phosphorus oxychloride, at least about one mole of phosphorus trichloride, and at least about one mole of trialkylamine compound per mole of hydroxy substituent in the hydroxypyrimidine compound to be converted to chloro substituent.

The function of the phosphorus oxychloride in the reaction mixture is to convert the hydroxy substituents of the pyrimidine compound starting material into chloro substituents and to help keep the mixture fluid. It is often more preferred to use about 1.3 to about 1.7 mole of phosphorus oxychloride per mole of hydroxy substituent in the hydroxypyrimidine starting material and most preferred to use about 1.5 mole.

The function of the phosphorus trichloride in the reaction mixture is initially as a solvent or diluent to help keep the mixture fluid. Phosphorus trichloride is especially useful for this purpose because it can later be used as a reagent in the preferred recovery method for the chloropyrimidine product (to convert the chlorophosphoric acids and any hydrides to phosphorus oxychloride for recycle) and its use avoids the necessity of having either a large excess of phosphorus oxychloride or additional solvents in the reaction mixture. The amount of phosphorus trichloride added is at least about 1 mole per mole of hydroxy substituent in the hydroxypyrimidine starting material. Preferably, from about 1.0 to about 1.2 mole is used and most preferably, about 1.01 to about 1.05 mole is used. The addition of an excess of phosphorus trichloride is not believed to be harmful to the process, but is generally avoided from an economic point of view. If less than one mole of phosphorus trichloride is used, not all of the chlorophosphoric acid by-products will be converted to phosphorus oxychloride in the optional recovery aspect of the process, which is described below, and related recovery methods.

The amount of trialkylamine compound added is generally an amount sufficient to react with essentially all of the acid produced in the reaction and to catalyze the reaction. About one mole of trialkylamine compound per mole of hydroxy substituent being converted to chloro substituent is required to achieve this objective. Amounts of trialkylamine compound in excess of about two moles per mole of hydroxy substituent being converted to chloro substituent do not generally improve the process and are contraindicated Suitable trialkylamine compounds include those of Formula III:

wherein each R independently represents a $C_1$–$C_8$ alkyl group with the proviso that the compound contains no more than about 15 carbon atoms. The term alkyl as used herein includes branched chain and cyclic forms. Suitable trialkylamine compounds include triethylamine, tributylamine, dibutylethylamine, hexyldimethylamine, and the like. Triethylamine is typically preferred.

The chemical reaction of the process is generally carried out at a temperature sufficiently high to promote a usefully fast reaction rate up to the boiling point of the reaction mixture. Temperatures of about 40° C. to about 100° C. are generally preferred. Temperatures of about 40° C. to about 80° C. are typically more preferred. The process is further carried out with effective agitation to ensure good mixing and, generally, with means for excluding moisture. The process is preferably carried out at atmospheric pressure, but can be carried out at pressures above atmospheric.

It is typically preferred to carry out the preparative aspect of the invention in multiple segments as a means of minimizing the amount phosphorus oxychloride needed to maintain fluidity and mixing. For example, the reaction is preferably carried out by the consecutive steps of a) combining 20 to 80 percent of the total amount of hydroxypyrimidine compound used with the phosphorus oxychloride and phosphorus trichloride, b) adding the same percentage as in a) of the total amount of trialkylamine compound used and allowing the mixture to react for a period, c) adding another percentage of the total amount of hydroxypyrimidine compound used, d) adding the same percentage as in c) of the total amount of trialkylamine compound used and allowing the mixture to react for a period, and e) repeating steps c) and d) until the total amounts of the hydroxypyrimidine and trialkylamine compound have been added. The reaction period in steps b) and d) is a sufficient amount of time for the reaction to proceed that the viscosity of the reaction mixture slurry is significantly reduced. The reaction period in the final performance of step d) is an amount of time sufficient for the reaction to proceed substantially to completion. Reaction periods of 1 to 8 hours, usually 2 to 4 hours, are generally sufficient.

In the multiple segment embodiment of the invention, the fraction of hydroxypyrimidine compound and of the trialkylamine added in the first segment is typically a fraction that will result in as concentrated a solution of these reagents as possible while maintaining sufficient fluidity to permit adequate mixing and heat transfer in the mixture. It is typically more preferred to add about 40 to about 65 percent of the total amount of the hydroxypyrimidine compound and of the total amount of the trialkylamine compound in steps a) and b) and the remaining percentage of the total of each in a single performance of subsequent steps c) and d). It is typically most preferred to add about 45 to about 60 percent of the total amount in steps a) and b) and the remainder in a single performance of subsequent steps c) and d). It is often advantageous to cool the reactor after completion of step b) in order reduce the phosphorus oxychloride and phosphorus trichloride vapors during the hydroxypyrimidine compound addition in step c). It is also often advantageous to add the trialkylamine compound in steps b) and d) slowly rather than all at once.

The recovery aspect of the process of the invention is especially suitable for the recovery of low melting chloropyrimidine compounds of Formula I:

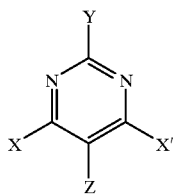

wherein X and X' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl with the proviso that at least one X and X' represents Cl; Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br from the mixture obtained by the reaction of an hydroxypyrimidine compound of Formula II:

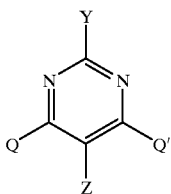

wherein Q and Q' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, Cl, or OH with the proviso that at least one of Q and Q' represents OH; Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br which was prepared by the reaction of phosphorus oxychloride and a trialkylamine compound of Formula III:

wherein each R independently represents a $C_1$–$C_8$ alkyl group and said trialkylamine compound contains up to about 15 carbon atoms. That is, the process is especially useful for the recovery of chloropyrimidine compounds prepared using preparative aspects of the process of the invention as described hereinabove and related processes.

The recovery process involves the consecutive steps of a) converting the by-product chlorophosphoric acids in said mixture to phosphorus oxychloride by reaction with phosphorus trichloride, which is present as a solvent or diluent or is added, and chlorine at about 30° C. to about 150° C. and subsequently b) adding a supplemental amount of the chloropyrimidine compound being recovered and removing phosphorus oxychloride by distillation, c) combining the distillation residue with water and an alkali metal hydroxide base to obtain a two liquid phase system, the aqueous phase of which has a pKa of about 11 or higher, d) removing the trialkylamine compound by distillation, and e) removing the aqueous phase.

The conversion of by-product chlorophosphoric acids to phosphorus oxychloride by reaction with phosphorus trichloride and chlorine is well-established in the art. Phosphorus pentachloride is generally believed to be formed first and to be the true reactant. The phosphorus trichloride that reacts is eventually converted to phosphorus oxychloride.

The advantage of this reaction in the present invention is that essentially all of the phosphorus containing compounds used in the process can be recovered as phosphorus oxychloride. The overall process of the invention utilizes phosphorus oxychloride as a reagent, but it is a net producer of this compound. Hydrogen chloride in the form of the hydrochloride salt of the trialkylamine compound employed is also produced. The reaction is generally carried out by heating the reaction mixture and adding chlorine to it. The reaction is generally carried out at about 30° C. to about 150° C. and is often preferably carried out at about 40° C. to about 80° C. The reaction mixture is preferably agitated to achieve good mixing. Chlorine is typically added as a gas, often with dispersion and under the surface of the liquid reaction mixture.

The addition of supplemental amounts of the chloropyrimidine compound produced to the mixture is done to ensure that the mixture remains fluid after the phosphorus oxychloride and any residual phosphorus trichloride are removed by distillation. Sufficient chloropyrimidine compound is added to achieve that objective. Typically an amount of chloropyrimidine compound between about 0.3 and about 2.0 times the amount produced in the process is added. Preferably, an amount of the chlorpyrimidine compound approximately equal to that produced in the process is added. The chloropyrimidine compound can be added either before or during the distillation or portions can be added both before and during the distillation. A portion of the supplemental chloropyrimidine compound can, further, be added after the distillation. The distillation to remove phosphorus oxychloride and any residual phosphorus trichloride can be carried out at atmospheric pressure or under reduced pressure. It is preferably carried out under reduced pressure.

The water and alkali metal hydroxide that are combined with the distillation residue in step c) are combined slowly with agitation. The water involved can be combined separately or as a part of an aqueous alkali metal hydroxide solution. It is typically combined separately and before the alkali metal hydroxide. Sufficient alkali metal hydroxide is used to convert essentially all of the trialkylamine hydrochloride compound present to free trialkylamine compound. A pH above about 11 is generally sufficient to accomplish this objective and a pH above about 12 is essentially always sufficient. The minimum pH that will accomplish this objective is a function of the pKa of the trialkylamine hydrochloride salt present. A large excess of alkali metal hydroxide compound is generally not desirable as it may cause decomposition of the chloropyrimidine product. Sodium hydroxide and potassium hydroxide are generally preferred alkali metal hydroxide compounds. Typically, sufficient water is first combined with the distillation residue to dissolve the trialkylamine salts present and then a concentrated aqueous alkali metal hydroxide solution is added to neutralize the trialkylamine hydrochloride compound. This procedure facilitates the complete neutralization of the trialkylamine hydrochloride compound. Especially on a larger scale, it is generally preferred to add the distillation residue to the water in order to control the exotherm that is normally experienced. The temperature of this mixture is best kept below about 70° C. to minimize hydrolytic decomposition of the chloropyrimidine product. Cooling is often applied to the reaction vessel to accomplish this objective.

Chloropyrimidine compounds of Formula I wherein Y also represents chloro are especially susceptible to hydrolytic decomposition in this aqueous alkaline media and when such compounds appear as impurities in the preparation of a chloropyrimidine compound wherein Y is other than chloro, they can sometimes be removed by allowing a limited amount of decomposition to take place. For example, any by-product 2,4,6-trichloropyrimidine formed in the preparation of 4,6-dichloro-2-ethoxypyrimidine from 4,6-dihydroxy-2-ethoxypyrimidine by reaction with phosphorus oxychloride is typically made water soluble by partial hydrolytic decomposition during the recovery steps. The water soluble degradate is then removed from the desired 4,6-dichloro-2-ethoxypyrimidine when the aqueous phase is removed from the organic phase in step e) of the recovery aspect of the process.

The two liquid phase mixture obtained in step c) is distilled to remove the trialkylamine compound generated by the addition of alkali metal hydroxide. Some of the water present is usually also removed as distillate. The distillation of step d) can be carried out at atmospheric pressure or under reduced pressure, but is typically carried out under reduced pressure. Pressures below about 100 mm Hg (13 kilopascals), which result in distillation pot temperatures below about 60° C. are generally more preferred. The mixture is generally agitated during the distillation for better temperature control. The hydrolytic decomposition discussed for step c) of the recovery process apply to step d) as well. Any chloropyrimidine compound of Formula I that is removed by co-distillation with the water can be recovered as an insoluble (in water) oil and recycled into a later distillation or to a later step b). The trialkylamine compound removed by distillation is typically recovered for recycle as a reagent in the preparative aspect of the invention.

The two liquid phase residue from the distillation of step d) is separated into an aqueous phase and an organic phase in step e) by standard techniques, such as by decantation. A supplemental amount of water is sometimes added before this separation to facilitate the formation of two continuous phases.

The organic phase obtained by the procedure described above is primarily the desired chloropyrimidine compound of Formula I. This crude product is generally about 87 to about 97 percent pure and can be used directly, without further purification, as an intermediate or an end-use product. Alternatively, it can be purified by any of the methods known in the art to purify high boiling, water-insoluble liquids or low melting solids. For example, the crude product can be extracted with water, dilute aqueous acids, dilute aqueous bases, or organic solvents in which it is insoluble, can be dried by heating under reduced pressure, by azeotropic distillation, or by contacting with a hydroscopic solid, can be distilled under reduced pressure, or can be chromatographed.

It is generally preferred to employ both the preparative and the recovery aspects of the process of the invention in concert. An overall recovered yield of chloropyrimidine compound of Formula I of about 75 to about 95 percent of theory can be achieved.

EXAMPLES

1. Preparation of 4,6-Dichloro-2-ethoxypyrimidine

A 1.5 L (liter) glass reactor equipped with a circulated liquid heating jacket, a mechanical stirrer, condenser, solids addition tube with a teflon screw feeder, liquid addition tube, and nitrogen inlet and outlet was purged with nitrogen and loaded with 461 g (grams) (3.00 mol (mole)) of phosphorus oxychloride and 274 g (2.00 mol) of phosphorus trichloride. To this was added 82.2 g (0.50 mol) of 2-ethoxy-4,6-dihydroxypyrimidine through the solids addition tube over a 17-min period with stirring. The reactor was heated to 50°

C. by means of the heating jacket and 101 g (1.00 mol) of triethylamine was added through the liquid addition tube over a 49-min period. The mixture, which became thick and cloudy at first, became clear and then translucent; the temperature rose to about 58° C. The mixture was allowed to react another 107 min with the heating jacket at 50° C. The reactor was cooled to 19° C. over an 87-min period and another 82.2 g (0.50 mol) of 2-ethoxy-4,6-dihydroxypyrimidine was added over a 14-min period with stirring. The reactor was heated to 45° C. and another 101 g (1.00 mol) of triethylamine was added over a 46-min period. The temperature rose to 55° C. The mixture, which remained fluid, was heated to 75° C. with stirring for 4 hours and was then allowed to cool to ambient temperature and stir overnight. Analysis of the reaction mixture by quantitative liquid chromatography showed the reaction to be complete.

The reaction mixture was heated to 65° C. and 142 g (2.00 mol) of chlorine was added under the surface of the reaction mass over a 98-min period with stirring. The temperature was reduced to 50° C. and the mixture was allowed to react overnight. The condenser was replaced with a distillation head and the mixture was simple distilled with stirring under a pressure of 50 mm Hg (millimeters of mercury)(6.7 kilopascals) to remove about 508 g of phosphorus oxychloride. A 197 g portion of dry, 93.3 percent purity 4,6-dichloro-2-ethoxypyrimidine was added to the distillation residue and distillation continued under 34 mm Hg (4.5 kilopascals) pressure to remove another 160 g of phosphorus oxychloride.

The distillation residue was cooled to 50° C. and 412 g of water was added slowly with stirring. There was an exotherm at the start of the addition and two liquid phases formed. A 478 g (1.23 mol) amount of a 45 percent aqueous solution of potassium hydroxide was then added dropwise over a 45 min period with stirring. The resulting mixture was split into two approximately equal portions and a first 808 g portion (301 g (50.6 percent) of organic phase) was distilled in a five plate Oldershaw column under 86 mm Hg (11.4 kilopascals) pressure to remove 188 g of water and about 80.2 g of triethylamine. The residue was diluted with 205 g of water and the phases separated to obtain 187 g of organic phase that was found to be 92.3 percent purity 4,6-dichloro-2-ethoxypyrimidine (81 percent of theory). This was filtered through a sintered glass filter to remove a few particulates. The second portion was treated similarly to obtain 158 g of 89.1 percent purity 4,6-dichloro-2-ethoxypyrimidine (77 percent of theory).

2. 4,6-Dichloro-2-ethoxypyrimidine Recovery 4,6-Dichloro-2-ethoxypyrimidine was prepared from 4,6-dihydroxy-2-ethoxypyrimidine essentially as described in Example 1 and the distillation residue obtained after conversion of the chlorophosphoric acid by-products to phosphorus oxychloride and distillation of the reaction mixture to remove the phosphorus oxychloride was analyzed by liquid phase chromatography. The components of the distillation residue observed by ultraviolet absorption detection were found to include about 91.8 percent the desired product and about 4.1 percent 2,4,6-trichloropyrimidine. The distillation residue was added to water with vigorous stirring. There was an exotherm. Sufficient 45 percent aqueous potassium hydroxide solution was then added with stirring to bring the pH of the aqueous phase of the mixture to 12.8, the pressure was reduced to about 80 mm Hg (about 11 kiloPascals), and the mixture was heated to 50° C. The triethylamine liberated by the addition of the potassium hydroxide was removed by distillation. The organic phase of the distillation residue was separated from the aqueous phase by decantation and was analyzed by liquid chromatography. It was found to be about 96.8 percent the title compound uncontaminated with 2,4,6-trichloropyrimidine, which was not detected.

What is claimed is:

1. A process for the preparation of a chloropyrimidine compound of the formula:

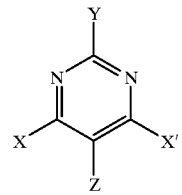

wherein

X and X' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl with the proviso that at least one X and X' represents Cl;

Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br which comprises contacting an hydroxypyrimidine compound of the formula:

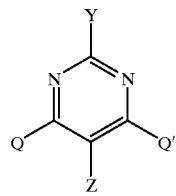

wherein

Q and Q' each, independently represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, Cl, or OH with the proviso that at least one of Q and Q' represents OH;

Y represents $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, or Cl; and Z represents H, $C_1$–$C_4$ alkyl, $C_1$–$C_4$ fluoroalkyl, $C_1$–$C_4$ alkoxy, $C_1$–$C_4$ fluoroalkoxy, $C_1$–$C_4$ alkylthio, CN, F, Cl, or Br with, based on the number of moles of hydroxy group in the hydroxypyrimidine compound, at least about one to about two moles of phosphorus oxychloride, at least about one mole of phosphorus trichloride, and at least about one mole of a trialkylamine compound of Formula III:

$R_3N$ wherein each R independently represents a $C_1$–$C_8$ alkyl group and said trialkylamine compound contains up to about 15 carbon atoms and heating.

2. A process according to claim 1 wherein about 1.3 to about 1.7 mole of phosphorus oxychloride is used per mole of hydroxy group in the hydroxypyrimidine compound.

3. A process according to claim 1 wherein about 1.0 to about 1.2 mole of phosphorus trichloride is used per mole of hydroxy group in the hydroxypyrimidine compound.

4. A process according to claim 1 wherein the trialkylamine compound is triethylamine.

5. A process according to claim 1 wherein the reaction mixture is heated in the range of about 40° C. to about 100° C.

6. A process according to claim 1 wherein, in the chloropyrimidine compound, one of X and X' represents chloro and the other represents chloro or methyl; Y represents methoxy or ethoxy; and Z represents fluoro or hydrogen.

7. A process according to claim 6 wherein the hydroxypyrimidine compound is 2-ethoxy-4,6-dihydroxypyrimidine and the chloropyrimidine compound is 4,6-dichloro-2-ethoxypyrimidine.

8. A process according to claim 1 carried out by the consecutive steps of
   a) combining 20 to 80 percent of the total amount of hydroxypyrimidine compound used with the phosphorus oxychloride and phosphorus trichloride,
   b) adding the same percentage as in a) of the total amount of trialkylamine compound used and allowing the mixture to react for a period,
   c) adding another percentage of the total amount of hydroxypyrimidine compound used,
   d) adding the same percentage as in c) of the total amount of trialkylamine compound used and allowing the mixture to react for a period, and
   e) repeating steps c) and d) until the total amounts of hydroxypyrimidine and trialkylamine compound used have been added.

9. A process according to claim 8 wherein about 45 to about 60 percent of the total amount of the hydroxypyrimidine compound used and of the trialkylamine compound used is combined in steps a) and b).

10. A process according to claim 8 wherein about 1.3 to about 1.7 mole of phosphorus oxychloride and 1.0 to about 1.2 mole of phosphorus trichloride are used per mole of hydroxy group in the hydroxypyrimidine compound.

11. A process according to claim 8 wherein the trialkylamine compound is triethylamine.

12. A process according to claim 8 wherein the reaction mixture is heated in the range of about 40° C. to about 100° C.

13. A process according to claim 8 wherein, in the chloropyrimidine compound, one of X and X' represents chloro and the other represents chloro or methyl; Y represents methoxy or ethoxy; and Z represents fluoro or hydrogen.

14. A process according to claim 13 wherein the hydroxypyrimidine compound is 2-ethoxy-4,6-dihydroxypyrimidine and the chloropyrimidine compound is 4,6-dichloro-2-ethoxypyrimidine.

* * * * *